United States Patent
Hayashi et al.

(10) Patent No.: US 9,744,118 B2
(45) Date of Patent: Aug. 29, 2017

(54) TREATMENT AGENT AND COSMETIC COMPOSITION COMPRISING CO-MODIFIED ORGANOPOLYSILOXANE

(71) Applicant: DOW CORNING TORAY CO., LTD., Tokyo (JP)

(72) Inventors: Akito Hayashi, Chiba (JP); Seiji Hori, Fukui (JP); Tomohiro Iimura, Chiba (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 0 days.

(21) Appl. No.: 14/433,196

(22) PCT Filed: Oct. 2, 2013

(86) PCT No.: PCT/JP2013/076826
§ 371 (c)(1),
(2) Date: Apr. 2, 2015

(87) PCT Pub. No.: WO2014/054693
PCT Pub. Date: Apr. 10, 2014

(65) Prior Publication Data
US 2015/0272858 A1 Oct. 1, 2015

(30) Foreign Application Priority Data

Oct. 2, 2012 (JP) .................. 2012-220286

(51) Int. Cl.
| | | |
|---|---|---|
| *A61Q 1/02* | (2006.01) | |
| *A61Q 1/12* | (2006.01) | |
| *A61K 8/27* | (2006.01) | |
| *A61K 8/29* | (2006.01) | |
| *A61K 8/04* | (2006.01) | |
| *A61K 8/894* | (2006.01) | |
| *A61Q 1/04* | (2006.01) | |
| *A61Q 1/06* | (2006.01) | |
| *A61Q 1/10* | (2006.01) | |
| *A61Q 17/04* | (2006.01) | |
| *A61K 47/44* | (2017.01) | |
| *C08G 77/46* | (2006.01) | |
| *A61Q 15/00* | (2006.01) | |
| *A61Q 19/00* | (2006.01) | |
| *C09D 183/12* | (2006.01) | |
| *C08L 83/12* | (2006.01) | |
| *A61K 8/02* | (2006.01) | |
| *A61K 8/31* | (2006.01) | |
| *A61K 8/891* | (2006.01) | |
| *A61Q 1/08* | (2006.01) | |

(52) U.S. Cl.
CPC ............ *A61K 8/894* (2013.01); *A61K 8/0241* (2013.01); *A61K 8/04* (2013.01); *A61K 8/27* (2013.01); *A61K 8/29* (2013.01); *A61K 8/31* (2013.01); *A61K 8/891* (2013.01); *A61K 47/44* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 1/12* (2013.01); *A61Q 15/00* (2013.01); *A61Q 17/04* (2013.01); *A61Q 19/00* (2013.01); *A61Q 19/002* (2013.01); *C08G 77/46* (2013.01); *C08L 83/12* (2013.01); *C09D 183/12* (2013.01); *A61K 2800/413* (2013.01); *A61K 2800/42* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 4,698,178 A | 10/1987 | Huttinger et al. | |
| 6,017,546 A | 1/2000 | Glover | |
| 6,045,781 A | 4/2000 | Bungard et al. | |
| 6,235,275 B1 * | 5/2001 | Chen | A61K 8/0295 424/401 |
| 6,342,239 B1 | 1/2002 | Tachibana et al. | |
| 2003/0185771 A1 | 10/2003 | Kamei et al. | |
| 2005/0008592 A1 * | 1/2005 | Gardel | A61K 8/06 424/63 |
| 2011/0182846 A1 | 7/2011 | Ikeda et al. | |
| 2012/0251605 A1 | 10/2012 | Iimura et al. | |
| 2012/0263662 A1 | 10/2012 | Iimura et al. | |

(Continued)

FOREIGN PATENT DOCUMENTS

| | | |
|---|---|---|
| CN | 1230398 A | 10/1999 |
| JP | S61-90732 A | 5/1986 |

(Continued)

OTHER PUBLICATIONS

PCT/JP2013/076811 International Search Report dated Dec. 24, 2013, 3 pages. (In Japanese).
English language abstract for JP62-054759A extracted from https://www4.j-platpat.inpit.go.jp database on Jun. 23, 2015, 2 pages.
English language abstract and machine assisted English translation for JPH07-053326A extracted from https://www4.j-platpat.inpit.go.jp database on Jun. 15, 2015, 11 pages.
English language abstract and machine assisted English translation for JPH08-027274A extracted from https://www4.j-platpat.inpit.go.jp database on Jun. 22, 2015, 25 pages.
English language abstract and machine assisted English translation for JPH10-167946A extracted from https://www4.j-platpat.inpit.go.jp database on Jun. 8, 2015, 13 pages.

(Continued)

*Primary Examiner* — Abigail Fisher
(74) *Attorney, Agent, or Firm* — Warner Norcross & Judd LLP

(57) ABSTRACT

A surface treatment agent or a powder treatment agent comprising a co-modified organopolysiloxane is disclosed. The co-modified organopolysiloxane is represented by the general formula: $R^1_a R^2_b Q_c SiO_{(4-a-b-c)/2}$. The co-modified organopolysiloxane has a number average molecular weight of less than 4500 and includes a long-chain alkyl group and a polyoxyalkylene group in the molecule.

20 Claims, No Drawings

(56) References Cited

U.S. PATENT DOCUMENTS

| | | |
|---|---|---|
| 2012/0269747 A1 | 10/2012 | Iimura et al. |
| 2012/0269875 A1 | 10/2012 | Tamura et al. |
| 2013/0096206 A1 | 4/2013 | Iimura et al. |
| 2013/0102686 A1 | 4/2013 | Tamura et al. |
| 2013/0210930 A1 | 8/2013 | Souda et al. |
| 2014/0004065 A1 | 1/2014 | Souda et al. |
| 2014/0371330 A1 | 12/2014 | Hayashi et al. |

FOREIGN PATENT DOCUMENTS

| | | | |
|---|---|---|---|
| JP | S6190732 | A | 5/1986 |
| JP | S62-54759 | A | 3/1987 |
| JP | S6254759 | A | 3/1987 |
| JP | H07-053326 | A | 2/1995 |
| JP | H0769860 | A | 3/1995 |
| JP | 07206637 | A * | 8/1995 |
| JP | H08-027274 | A | 1/1996 |
| JP | H0827274 | A | 1/1996 |
| JP | H10-167946 | A | 6/1998 |
| JP | H11-349466 | A | 12/1999 |
| JP | H11349466 | A | 12/1999 |
| JP | 2002-38013 | A | 2/2002 |
| JP | 2007254538 | A | 10/2007 |
| JP | 2011-148784 | A | 8/2011 |
| JP | 2011-149017 | A | 8/2011 |
| JP | 2011-246704 | A | 12/2011 |
| JP | 2011-246705 | A | 12/2011 |
| JP | 2011-246706 | A | 12/2011 |
| JP | 2012-149052 | A | 8/2012 |
| JP | 2013-151657 | A | 8/2013 |
| WO | WO2007/109240 | A2 | 9/2007 |
| WO | WO2009/006091 | A2 | 1/2009 |
| WO | WO2009/022621 | A1 | 2/2009 |
| WO | WO2011/028765 | A1 | 3/2011 |
| WO | WO2011/028770 | A1 | 3/2011 |
| WO | WO2011/049246 | A1 | 4/2011 |
| WO | WO2011049248 | A1 | 4/2011 |
| WO | WO2011/136394 | A1 | 11/2011 |

OTHER PUBLICATIONS

English language abstract and machine assisted English translation for JPH11-349466A extracted from https://www4.j-platpat.inpit.go.jp database on Jun. 22, 2015, 13 pages.

English language abstract for JP2007254538A extracted from https://www4.j-platpat.inpit.go.jp database on May 7, 2015, 2 pages.

English language abstract for JPS6254759A extracted from http://worldwide.espacenet.com on Apr. 28, 2016, 2 pages.

English language abstract and machine-assisted English translation for JPH0827274A extracted from http://worldwide.espacenet.com on Apr. 28, 2016, 20 pages.

English language abstract and machine-assisted English translation for JP2007254538A extracted from http://worldwide.espacenet.com on Apr. 28, 2016, 50 pages.

PCT/JP2013/076811 International Search Report dated Dec. 24, 2013, 2 pages. (In English).

* cited by examiner

TREATMENT AGENT AND COSMETIC COMPOSITION COMPRISING CO-MODIFIED ORGANOPOLYSILOXANE

CROSS-REFERENCE TO RELATED APPLICATIONS

This application is the National Stage of International Patent Application No. PCT/JP2013/076826, filed on Oct. 2, 2013, which claims priority to and all advantages of Japanese Patent Application No. 2012-220286, filed on Oct. 2, 2012, the content of which is hereby incorporated by reference.

TECHNICAL FIELD

The present invention relates to a co-modified organopolysiloxane copolymer having a number average molecular weight of less than 4500 and having a long-chain alkyl group and a polyether group in the molecule; and a surfactant or surface treatment agent—in particular, a powder treatment agent—containing the same. Additionally, the present invention relates to a powder that is surface treated using the powder treatment agent, a powder composition comprising the co-modified organopolysiloxane copolymer, and a powder-in-oil dispersion comprising an oil agent; and, moreover a preparation for external use, particularly a make-up cosmetic composition, comprising the same.

BACKGROUND ART

Various powders exemplified by white and colored pigments such as titanium oxide, zinc oxide, red iron oxide, and the like and extender pigments such as mica, sericite, and the like are widely used in the fields of basic cosmetic compositions and other various cosmetic compositions such as sunscreens, nail colors, nail coats, foundations, mascaras, eye liners, and the like. However, untreated powder is prone to agglomerate due to the electric charge and polarity, trace amount of impurities, and the like on the powder surface. Therefore, powders that have been subject to various surface treatments are widely used for the purpose of enhancing dispersibility and stability of a powder in a cosmetic composition and also improving the tactile sensation, moisture resistance, sebum resistance, and the like of a cosmetic composition comprising a powder.

Known examples of such surface treatments include lipophilization treatments using an oil agent, a metal soap, or the like; hydrophilization treatments using a surfactant, water-soluble polymer, or the like; hydrophobization treatments using silicone compounds; silica treatments; alumina treatments; and the like. Particularly, in recent years, there have been many cases where a surface treatment using a silicone compound having a reactive moiety in the molecule has been performed. The reactive site forms a chemical bond with the powder surface and, as a result, surface treatment using the silicone compound is effective from the perspective of simultaneously modifying the surface of the powder and blocking the surface activity of the powder without substantially changing the characteristics of the powder itself. In addition, because surface treatment can be performed reliably, the treatment agent will not separate from the powder surface, even when compounded in a cosmetic composition comprising a solvent. An example of such a surface treatment is a method in which a powder is surface treated using a methylhydrogenpolysiloxane (Patent Document 1). However, in this method, unreacted Si—H groups still remain even after the surface treating of the powder and, therefore, there is a problem when this powder is compounded in a cosmetic composition because hydrogen gas may be produced depending on the components and the like in the cosmetic composition.

On the other hand, methods for manufacturing a powder dispersion using a hydrophilic modified organopolysiloxane that has good compatibility with the powder surface have been proposed. Examples thereof include a method for forming a polyether-modified organopolysiloxane into a powder dispersing aid (Patent Document 2) and a method for forming an organopolysiloxane modified by polyglycerine or a similar polyhydric alcohol into a powder dispersing aid (Patent Document 3). However, there are problems in that the powder dispersion effectiveness is still insufficient, viscosity of a power dispersion obtained by dispersing a powder in silicone oil or a similar oil agent increases gradually over time, fluidity is lost, and the like.

As a method to resolve the problems described above, the present applicant has proposed methods using a co-modified organopolysiloxane copolymer having a group that has a carbosiloxy dendron structure and a glycerin derivative, polyhydric alcohol, or similar hydrophilic group in the molecule (Patent Documents 4, 5 and 6). Such co-modified organopolysiloxanes are safe and do not produce hydrogen, and can be advantageously used in the surface treating of a powder. Moreover, affinity with other raw materials of cosmetic compositions is superior, and the dispersibility and stability of the powder in a cosmetic composition comprising a powder can be enhanced.

In general, in formulations primarily containing a silicone as an oil agent, the feel is sometimes too light due to the characteristics of the silicone. However, in order to meet the wide-ranging needs of consumers, it is necessary to prepare cosmetic compositions having a variety of feels, and formulations having a heavy feel are also sometimes preferable in order to give an impression of elegance, in particular. In the preparation of such agents, formulations based on various hydrocarbon solvents such as oil agents other than silicone including isododecane, for example, are also being actively developed. However, the co-modified organopolysiloxane described above has a molecular design primarily suited to a silicone-based formulations, so there is a problem in that the co-modified organopolysiloxane does not demonstrate the desired dispersibility in hydrocarbon solvents. Accordingly, the development of silicone-based active agents and dispersants compatible with hydrocarbon solvents has become extremely important.

In order to solve the problems described above, there are alkyl-modified silicone polyethers, which are also advantageous from the perspective of cost (Patent Document 7). The co-modified organopolysiloxane copolymers described above are not only used as emulsifiers, but are also used as dispersants and are applied to various powder cosmetic compositions. However, all of these copolymers have a relatively high molecular weight and a large number of hydrophilic groups, so there are problems in that the dispersibility with respect to fine particle powders is low, and the copolymers tend to become sticky when included in formulations.

PRIOR ART DOCUMENTS

Patent Documents

Patent Document 1: Japanese Unexamined Patent Application Publication No. H07-53326A (Japanese Patent No. 2719303B)

Patent Document 2: Japanese Unexamined Patent Application Publication No. H10-167946A
Patent Document 3: Japanese Unexamined Patent Application Publication No. 2002-038013A
Patent Document 4: WO/2011/049246
Patent Document 5: WO/2011/049248
Patent Document 6: WO/2011/136394
Patent Document 7: Japanese Unexamined Patent Application Publication No. S61-90732A

SUMMARY OF INVENTION

Technical Problem

An object of the present invention is to provide a co-modified organopolysiloxane by which the problems described above can be resolved. More specifically, an object of the present invention is to provide a co-modified organopolysiloxane which, in comparison to conventional co-modified silicones, has high powder dispersibility and excellent compatibility with a wide variety of hydrocarbon solvents and can be advantageously used as a cosmetic raw material. A second object of the present invention is to provide a powder treatment agent comprising the organopolysiloxane, a powder that is surface treated using the powder treatment agent, a powder composition comprising the co-modified organopolysiloxane copolymer, and a powder-in-oil dispersion comprising an oil agent; and, moreover an external use preparation, particularly a make-up cosmetic composition, comprising the same.

Solution to Problem

As a result of intensive investigation aimed at achieving the above objects, the present inventors arrived at the present invention. That is, the object of the present invention is achieved by an alkyl-modified silicone polyether having a number average molecular weight of less than 4500. In the present invention, the "number average molecular weight" is the number average molecular weight in terms of polystyrene as measured by GPC (gel permeation chromatography) and may be simply described as the "number average molecular weight" hereinafter unless specified otherwise.

In addition, the object of the present invention is achieved by a surface treatment agent—a powder treatment agent, in particular—containing the alkyl-modified silicone polyether. Further, the object of the present invention is achieved by a powder that is surface treated using the powder treatment agent, a powder composition comprising the co-modified organopolysiloxane copolymer, a powder-in-oil dispersion comprising an oil agent, and a preparation for external use—a makeup cosmetic composition, in particular—comprising the same.

Specifically, the object described above is achieved by:
"[1] A surface treatment agent or powder treatment agent represented by general formula (1) below:

containing the co-modified organopolysiloxane having a number average molecular weight of less than 4500 in terms of polystyrene as measured by GPC (gel permeation chromatography) and having a long-chain alkyl group and a polyoxyalkylene group in the molecule. in the general formula (1),
$R^1$ is a substituted or unsubstituted monovalent hydrocarbon group having from 1 to 30 carbons, or a hydrogen atom;

$R^2$ is a substituted or unsubstituted long-chain or branched monovalent hydrocarbon having from 6 to 30 carbons; and Q is a hydrophilic group containing the polyoxyalkylene group represented by the following structural formula (2).

(wherein $R^3$ is an alkyl group having from 1 to 4 carbons or a hydrogen atom; r is from 0 to 100; s is a number in a range of from 0 to 50; and "r+s" is a number in a range of from 3 to 100); a, b, and c are numbers in ranges so that $1.0 \leq a \leq 2.5$, $0.001 \leq b \leq 1.5$, and $0.001 \leq c \leq 1.5$.}

[2] The surface treatment agent or powder treatment agent according to [1], wherein the co-modified organopolysiloxane is represented by structural formula (1-1) below.

[Formula 1]

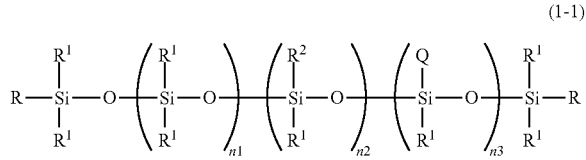

{In the formula, $R^1$, $R^2$, and Q are synonymous with the groups described above; and R is a group selected from $R^1$, $R^2$, and Q; however, when n3=0, at least one of the R moieties is Q; (n1+n2+n3) is a number in a range of from 2 to 40; n1 is a number in a range of from 1 to 30; n2 is a number in a range of from 1 to 20; and n3 is a number in a range of from 0 to 5.}

[3] The surface treatment agent or powder treatment agent according to [1] or [2], wherein the co-modified organopolysiloxane is represented by the following structural formula (1-1-1).

[Formula 2]

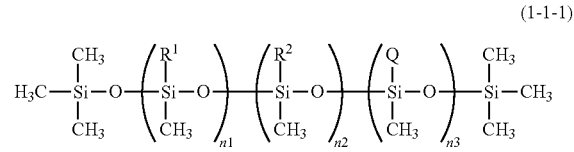

{In the formula, $R^1$, $R^2$, and Q are groups synonymous with the groups described above; (n1+n2+n3) is a number in a range of from 2.1 to 40; n1 is a number in a range of from 1 to 30; n2 is a number in a range of from 1 to 20; and n3 is a number in a range of from 0.1 to 5.}

[3-1] The surface treatment agent or powder treatment agent according to [3], wherein the co-modified organopolysiloxane is represented by the above structural formula (1-1-1), and the number average molecular weight thereof is in a range of from 2000 to 4450.

[4] A powder composition comprising: (A) the surface treatment agent or powder treatment agent described in any one of [1] to [3]; and
(B) a powder or a coloring agent.

[5] The powder composition according to [4], wherein the component (B) is one or two or more selected from the group consisting of an inorganic pigment powder, an organic pigment powder, and a resin powder, having an average diameter in a range of 1 nm to 20 μm.

[6] A powder-in-oil dispersion comprising: (A) the surface treatment agent or powder treatment agent described in any one of [1] to [3]; (B) a powder or coloring agent; and (C) one or more oil agents selected from a silicone oil, a nonpolar organic compound, or a low-polarity organic compound that is a liquid at 5 to 100° C.

[7] A powder-in-oil dispersion comprising: (A) the surface treatment agent or powder treatment agent described in any one of [1] to [3]; (B) a powder or coloring agent; and (C1) a hydrocarbon oil that is liquid at 5 to 100° C.

[8] A preparation for external use containing the surface treatment agent or powder treatment agent described in any one of [1] to [3].

[9] The preparation for external use described in [8] that is a cosmetic composition or a medicament.

[10] A cosmetic composition comprising the powder composition according to [4] or [5].

[11] A cosmetic composition comprising the powder-in-oil dispersion described in [6] or [7].

[12] A powder composition comprising: (A) the surface treatment agent or powder treatment agent described in any one of [1] to [3];
(B) a powder or coloring agent; and
(C) a silicone oil, a nonpolar organic compound, or a low-polarity organic compound that is a liquid from 5 to 100° C."

Advantageous Effects of Invention

With the present invention, it is possible to provide a co-modified organopolysiloxane which, in comparison to conventional co-modified silicones, has a low molecular weight and therefore high powder dispersibility and excellent compatibility with a wide variety of hydrocarbon solvents and can be advantageously used as a cosmetic raw material. As a result, preparation of particularly a powder-in-oil dispersion is facilitated and, moreover, a product characterized by having superior powder dispersibility and stability can be provided. Additionally, according to the present invention, a powder treatment agent comprising the organopolysiloxane, a powder that is surface treated using the powder treatment agent, a powder composition comprising the co-modified organopolysiloxane copolymer, and a powder-in-oil dispersion comprising an oil agent; and, moreover a preparation for external use, particularly a make-up cosmetic composition can be provided. A variety of cosmetic compositions comprising the novel co-modified organopolysiloxane of the present invention can be provided. However, of these, a cosmetic composition using the powder-in-oil dispersion described above, particularly a make-up cosmetic composition can be advantageously provided.

DETAILED DESCRIPTION OF THE INVENTION

Hereinafter, the novel co-modified organopolysiloxane of the present invention, uses thereof as various types of treatment agents, and in particular, uses as a powder treatment agent and as a cosmetic raw material will be described in detail. Additionally, detailed descriptions of a powder-in-oil dispersion, an external use preparation, advantageously a cosmetic composition, and particularly advantageously a make-up cosmetic composition using the novel co-modified organopolysiloxane of the present invention will be given.

The co-modified organopolysiloxane according to the present invention is a co-modified organopolysiloxane having a long-chain alkyl group and a polyoxyalkylene group and having a number average molecular weight of less than 4500, and more specifically is a co-modified organopolysiloxane represented by the following general formula (1).

General Formula (1):

In general formula (1),
R$^1$ is a substituted or unsubstituted monovalent hydrocarbon group having from 1 to 30 carbons, or a hydrogen atom;
R$^2$ is a substituted or unsubstituted long-chain or branched monovalent hydrocarbon having from 6 to 30 carbons; and Q is a hydrophilic group containing the polyoxyalkylene group represented by the following structural formula (2).

General Formula (2):

In general formula (2), R$^3$ is an alkyl group having from 1 to 4 carbons or a hydrogen atom; r is from 0 to 100; s is a number in a range of from 0 to 50; and "r+s" is a number in a range of from 3 to 100.

In addition, a, b, and c are numbers in ranges so that $1.0 \leq a \leq 2.5$, $0.001 \leq b \leq 1.5$, and $0.001 \leq c \leq 1.5$.

The co-modified organopolysiloxane according to the present invention has a number average molecular weight of less than 4500 in terms of polystyrene as measured by GPC (gel permeation chromatography), preferably in a range of from 1000 to 4490, more preferably in a range of from 1500 to 4475, particularly preferably in a range of from 2000 to 4450, and most preferably in a range of from 3500 to 4400. When the number average molecular weight of the co-modified organopolysiloxane exceeds the upper limit described above, the performance becomes insufficient from the perspective of the powder dispersibility. More specifically, when the average molecular weight of the co-modified organopolysiloxane exceeds the upper limit described above, the resulting powder dispersion (in particular, a slurry, which is a powder-in-oil dispersion) thickens over time, which may make it difficult to use as a cosmetic raw material due to insufficient powder dispersion or, depending on the conditions, may make it absolutely impossible to prepare a powder dispersion.

In general formula (1), R$^1$ is a substituted or unsubstituted monovalent hydrocarbon group having from 1 to 30 carbons, or a hydrogen atom. However, R$^1$ is preferably independently an alkyl group having from 1 to 10 carbons or an aryl group, examples of which include straight-chain, branched, or cyclic alkyl groups such as methyl, ethyl, n-propyl, i-propyl, n-butyl, i-butyl, s-butyl, pentyl, neopentyl, cyclopentyl, and hexyl groups; and a phenyl groups. From a technical point of view, R$^1$ preferably is a methyl group or a phenyl groups. Additionally, R$^1$ may be a group wherein the hydrogen atoms bonded to the carbons of these groups are substituted at least partially by fluorine or a similar halogen atom, or by an organic group having an epoxy group, an acyl group, a carboxyl group, an amino group, a (meth)acryl group, a mercapto group, or the like.

R$^2$ is a substituted or unsubstituted long-chain or branched monovalent hydrocarbon group having from 6 to 30 carbons. Particularly, in cases where all of the R$^1$ moieties are alkyl groups having not more than 5 carbons (particularly methyl groups) or are phenyl groups, it is preferable that the long chain hydrocarbon group R$^2$ be comprised for the purpose of improving affinity with, particularly, hydrocarbon-based oil agents (i.e. cosmetic raw materials). Preferable examples of $R^2$ include alkyl groups having at least 6 carbons such as hexyl groups, heptyl groups, octyl groups, decyl groups, dodecyl groups, and hexadecyl groups; cycloalkyl groups such as cyclohexyl groups; aryl groups such as tolyl groups, xylyl groups, and naphthyl groups; and groups in which the hydrogen atoms bonded to the carbons of these groups are at least partially substituted with halogen atoms such as fluorine or organic groups such as epoxy groups, acyl groups, carboxyl groups, amino groups, methacrylic groups, and mercapto groups. Alkyl groups having from 8 to 20 carbons are preferable, and alkyl groups having from 12 to 20 carbons are even more preferable.

In general formula (1), Q is defined as a polyoxyalkylene group represented by the above general formula (2). Q is a portion which imparts hydrophilicity to the co-modified organopolysiloxane of this application and may be, for example, a group having a branched structure such as a branched polyoxyalkylene group.

In general formula (2), $R^3$ is an alkyl group having from 1 to 4 carbons or a hydrogen atom and is preferably a hydrogen atom.

In addition, r is a number in a range of from 0 to 100, and s is a number in a range of from 0 to 50.
Preferably, r is a number in a range of from 1 to 50, and s is a number in a range of from 0 to 40.
More preferably, r is a number in a range of from 2 to 40, and s is a number in a range of from 0 to 30.
Particularly preferably, r is a number in a range of from 3 to 30, and s is a number in a range of from 0 to 20.
In addition, "r+s" is a number in a range of from 3 to 100, preferably a number in a range of from 6 to 50, and more preferably a number in a range of from 8 to 40.

In general formula (1), a, b, and c are numbers in ranges so that $1.0 \leq a \leq 2.5$, $0.001 \leq b \leq 1$, and $0.001 \leq c \leq 1.5$. That is, when the co-modified organopolysiloxane according to the present invention has the aforementioned long-chain alkyl group and polyoxyalkylene group and has a number average molecular weight of less than 4500, it may assume the form of a straight-chain, branched, chain, cyclic, or reticular siloxane bond, but it is preferably a straight-chain or branched-chain co-modified organopolysiloxane from the perspective of being used as a powder treatment agent.

Preferable examples of the co-modified organopolysiloxane according to the present application include a straight co-modified organopolysiloxane represented by structural formula (1-1) below.

[Formula 3]

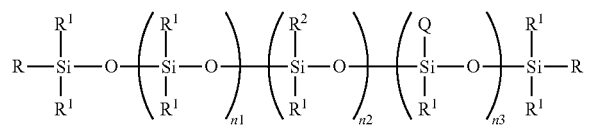

(1-1)

In the formula, $R^1$, $R^2$, and Q are synonymous with the groups described above; and R is a group selected from $R^1$, $R^2$, and Q. However, when n3=0, at least one of the R moieties is Q;

The straight-chain co-modified organopolysiloxane represented by the above structural formula (1-1) preferably has a number average molecular weight of less than 4500. Specifically, for n1 to n3 representing the average degree of polymerization of diorganosiloxane units, (n1+n2+n3) is a number in a range of from 2.1 to 40, preferably from 5 to 36, and more preferably from 10 to 30.

n1 is a number in a range of 1 to 30, preferably from 2 to 28, and more preferably from 3 to 25.

n2 is a number in a range of 1 to 20, preferably from 2 to 15, and more preferably from 3 to 10.

n3 is a number in a range of 0 to 5, preferably from 0.1 to 4, and more preferably from 0.2 to 3.

An industrially preferable example of the co-modified organopolysiloxane of the present application is a straight-chain co-modified organomethylpolysiloxane represented by the following structural formula (1-1-1).

[Formula 4]

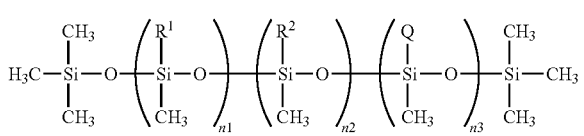

(1-1-1)

In the formula, $R^1$, $R^2$, and Q are groups synonymous with the groups described above, and n1 to n3 are synonymous with the numbers described above.

The co-modified organopolysiloxane according to the present application can be obtained by performing an addition reaction on a long-chain alkyl compound having one carbon-carbon double bond at one terminal of the molecular chain and a polyoxyalkylene compound having a reactive functional group such as an alkenyl group with respect to an organopolysiloxane having a reactive functional group such as Si—H. The type of addition reaction is not particularly limited, but from the standpoint of reaction control, purity, and yield, the addition reaction is preferably performed in the presence of a hydrosilylation reaction catalyst. In addition, a crude product of the co-modified organopolysiloxane obtained by an addition reaction may be purified by performing deodorizing treatment by means of a hydrogenation reaction in a solvent or without a solvent in the presence of a hydrogenation catalyst, or odor reduction treatment may be performed with an acidic substance. Further, a mixture with a polyoxyalkylene compound having a functional group such as an alkenyl group may be used.

In the synthesis of the co-modified organopolysiloxane according to the present application, a method common to the reaction, purification, and odor reduction treatment with an acidic substance disclosed by the applicants in paragraphs [0110] to [0122] of Patent Document 5 (WO/2011/049248) may be used.

Applications of the co-modified organopolysiloxane

The co-modified organopolysiloxane according to the present invention (also called "component (A)" hereinafter) is hydrophobic, has a long-chain alkyl group and a hydrophilic polyoxyalkylene group in the same molecule, and has a relatively low molecular weight, so the co-modified organopolysiloxane has excellent compounding stability with oleophilic raw materials—hydrocarbon solvents, in particular. Therefore, the co-modified organopolysiloxane is useful as various types of treatment agents and cosmetic raw material components and is extremely useful, in particular, as a surface treatment agent for use in a cosmetic and particularly as a powder treatment agent for use in the surface treatment of a powder or the dispersion of a powder.

Use as a Powder Treatment Agent

The co-modified organopolysiloxane according to the present invention has a relatively low molecular weight and be oriented on the surface of various powders so as to impart an appropriate degree of water repellency. Therefore, the co-modified organopolysiloxane according to the present invention can be suitably used as a powder surface treatment agent for the purpose of surface-treating or dispersing a cosmetic powder. Particularly, when used as a powder treatment agent, dispersion stability in a hydrocarbon solvent system of the co-modified organopolysiloxane according to the present invention is superior compared to conventional co-modified organopolysiloxanes. Thus, a powder-in-oil dispersion having superior stability in which the powder does not agglomerate or precipitate after preparing a powder composition obtained by treating the powder surface using a treatment agent can be provided, even when a method is used where the powder composition is dispersed in an oil agent dispersing medium and even when the powder is one where conventional powder treatment agents result in difficulties in stable dispersion.

The co-modified organopolysiloxane of the present invention has excellent compatibility with various other hydrophilic and hydrophobic components in the cosmetic composition, and can enhance the dispersibility and stability of a powder in a cosmetic composition that comprises a powder. Thus, the powder treatment agent of the present invention and the powder surface treatment agent of the present invention can improve the stability of a cosmetic composition that comprises a powder and can improve the uniform dispersibility of this powder. A cosmetic composition that comprises a powder that is surface treated using the powder surface treatment agent has high stability and this powder uniformly disperses in this cosmetic composition.

A compounded amount of the co-modified organopolysiloxane in the powder treatment agent of the present invention is not particularly limited provided that powder treatment effects are displayed and, for example, can be from 50 to 100 wt. % (mass %), and is preferably from 70 to 100 wt. %, and more preferably from 90 to 100 wt. %.

The powder treatment agent of the present invention may comprise a combination of the co-modified organopolysiloxane according to the present invention and another known surface treatment agent and be used to surface treat a powder. Examples of the other surface treatment agent include surface treatment agents based on methylhydrogenpolysiloxane, silicone resin, metal soap, silane coupling agents, silica, alumina, titanium oxide, and similar inorganic oxides; perfluoroalkylsilane, perfluoroalkyl phosphate ester salts, and similar fluorine compounds. Thus, the powder surface treatment agent of the present invention may, for example, comprise from 0.1 to 50 wt. % of the other surface treatment agent and preferably comprises from 1 to 30 wt. % and more preferably comprises from 5 to 10 wt. % of the other surface treatment agent.

When using the co-modified organopolysiloxane according to the present invention as a powder surface treatment agent, the compounded amount of the co-modified organopolysiloxane and the powder or coloring agent is preferably in a range of from 0.1 to 30 parts by mass and more preferably from 0.5 to 20 parts by mass per 100 parts by mass of the powder or coloring agent, and a range of from 1.5 to 15 parts by mass is particularly preferable. If the compounded amount is less than the lower limit described above, effects by the surface treating may be insufficient. On the other hand, even if the compounded amount exceeds the upper limit described above, greater prominent changes in texture will not occur, and the tendency for the powder and the co-modified organopolysiloxane to form a uniform mixture will increase.

The co-modified organopolysiloxane according to the present invention can be used to treat a powder surface using a conventional method. This method is not particularly limited and, for example, can be appropriately selected from the methods described below.

1. A method in which the target powder is surface treated by being dispersed in a medium selected from organic solvents in which the treatment agent has been compounded.
2. A method in which the powder is surface treated by mixing the powder and the powder treatment agent and, thereafter, crushing the mixture in a pulverizer such as a ball mill, a jet mill, or the like.
3. A treatment method in which the treatment agent is compounded in a solvent, the powder is dispersed in the mixture so as to adhere the treatment agent to the surface of the powder, and then the powder is dried and sintered.

Powder Composition

Additionally, the present invention relates to a powder composition comprising (A) the co-modified organopolysiloxane according to the present invention and (B) a powder or coloring agent. The powder composition can be obtained, according to the methods described above or the like, by mixing (B) the powder or coloring agent and (A) the co-modified organopolysiloxane according to the present invention, regardless of the purpose (i.e. to surface treat the powder, improve dispersibility of the powder, to act as a premix for a cosmetic raw material, or the like).

Powder-in-Oil Dispersion

Additionally, "powder-in-oil dispersion" as used in the present invention, refers to a product in which a powder composition obtained as described above is dispersed in an oil agent or, alternately, a product in which a co-modified organopolysiloxane is dissolved or dispersed in an oil agent, and then the powder is added by being mixed and dispersed therein; and a form thereof is that of a liquid dispersed product. This liquid dispersed product is also called a "slurry". In particular, the co-modified organopolysiloxane according to the present invention is useful in that a low-viscosity slurry can be prepared under the same conditions as those of the co-modified organopolysiloxane disclosed in the aforementioned Patent Document 5, even if it is an inorganic powder such as zinc oxide that cannot be sufficiently treated. In addition, the co-modified organopolysiloxane according to the present invention has a relatively low molecular weight and excellent compatibility and affinity with hydrocarbon oil agents such as isododecane or isohexadecane in comparison to conventionally known polyether-modified silicones. This yields the advantage that it is possible to prepare a powder-in-oil dispersion having excellent dispersion stability, stability over time, and compounding stability using a wide variety of cosmetic oil agents with which it was conventionally difficult to prepare a slurry.

The oil agent is not particularly limited provided that a liquid dispersion can be prepared, and is an oil agent that is commonly used as a component of a cosmetic composition. Furthermore, while the oil agent is typically liquid at room temperature, it may by solid such as a wax, and may also be in a highly viscous (high viscosity) gum-like state or paste-like state. The oil agent is preferably one or more selected from (C) a silicone oil, a nonpolar organic compound, and a low polarity organic compound that are liquid from 5 to 100° C.

The powder-in-oil dispersion of the present invention can be appropriately prepared according to a known method such as the methods described below.
1. A method in which the powder composition obtained as described above is added to and dispersed in an oil agent such as an ester oil or a hydrocarbon solvent.
2. A method in which the co-modified organopolysiloxane is dissolved or dispersed in the oil agent described above, the powder is added thereto, and the mixture is blended using a ball mill, a bead mill, a sand mill, or a similar disperser.

The obtained powder-in-oil dispersion can be compounded as-is in a preparation for external use (particularly in a cosmetic composition).

The powder composition and the powder-in-oil dispersion comprising the co-modified organopolysiloxane according to the present invention can be suitably used as a preparation for external use, particularly for a cosmetic composition or a cosmetic raw material.

(B) Powder or Coloring Agent

The powder or coloring agent (B) used in the powder composition, the powder-in-oil dispersion, and the like according to the present invention is a component that is commonly used in a cosmetic composition and includes white and colored pigments as well as extender pigments. The white and colored pigments are used to impart color and the like to the cosmetic composition, and the extender pigments are used to improve the tactile sensation and the like of the cosmetic composition. In the present invention, white and colored pigments as well as extender pigments commonly used in cosmetic compositions can be used as the powder without any particular restriction. In the present invention, preferably, one or two or more of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range of 1 nm to 100 μm. Particularly, when compounding the powder or coloring agent as a pigment, preferably one or two or more selected from an inorganic pigment powder, an organic pigment powder, and a resin powder having an average diameter in a range from 1 nm to 20 μm is compounded.

Examples of the powder include inorganic powders, organic powders, surfactant metal salt powders (metallic soaps), colored pigments, pearl pigments, metal powder pigments, and the like. Compounded products of these pigments can be used. Furthermore, the surfaces of these pigments may be water-repellent treated.

Specific examples include the same powders or colorants recited in paragraphs [0150] to [0152] of Patent Document 5 (WO2011/049248, filed by the present applicant).

The powders or coloring agents described above are preferably treated using other powder dispersants or surface treatment agents. In particular, the powders or coloring agents may be dispersed or surface-treated by the novel powder treatment agents and treatment methods proposed by the inventors of the invention of the present application in WO/2009/022621, Japanese Unexamined Patent Application Publication No. 2011-148784, Japanese Unexamined Patent Application Publication No. 2011-149017, Japanese Unexamined Patent Application Publication No. 2011-246704, Japanese Unexamined Patent Application Publication No. 2011-246705, Japanese Unexamined Patent Application Publication No. 2011-246706, WO/2009/022621, WO/2011/049246, WO/2011/049248, Japanese Patent Application 2011-286973, and the like, or treated to form a slurry using these novel powder treatment agents and the aforementioned oil agents. These novel treatment agents have an excellent improving effect on the unique texture and performance such as dispersion stability, so improving effects on the functionality, texture, storage stability, and the like of the cosmetic can be anticipated when used in combination with the novel cosmetic raw material of the present invention.

Of the powders recited, description of a silicone elastomer powder shall be given. The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the sidechain or the molecular terminal and a diorganopolysiloxane having an unsaturated hydrocarbon group such as an alkenyl group or the like on the sidechain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. In addition, by carrying out surface treatment using the co-modified organopolysiloxane, it is possible to impart a moist feeling to touch without reducing the suede-like feeling to touch of a silicone elastomer powder. Furthermore, when blending the co-modified organopolysiloxane in addition to a silicone elastomer powder in a cosmetic composition, it is possible to improve the dispersion stability of the powder in the overall cosmetic composition and obtain a cosmetic composition that is stable over time.

The silicone elastomer powder can be in various forms such as spherical, flat, amorphous, or the like. The silicone elastomer powder may also be in the form of an oil dispersion. With the cosmetic composition of the present invention, the silicone elastomer powder is particulate in form, and the primary particle size observed using an electron microscope and/or the average primary particle size measured by laser analysis or scattering is in a range from 0.1 to 50 μm. Additionally, a silicone elastomer powder having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or lower, and more preferably 65 or lower.

Of these silicone elastomer powders, specific examples of silicone elastomer spherical powders are the same as those disclosed by the applicants in paragraph [0168] of the above-mentioned Patent Document 5 (WO/2011/049248), and may be a silicone elastomer powder that has been subjected to a variety of water-repellent treatments, as disclosed in paragraphs [0150] to [0152].

The mixture of the co-modified organopolysiloxane (A) and the powder or coloring agent (B) is a form in which the powder is dispersed in the co-modified organopolysiloxane, and a compounded amount of the powder in the mixture is not particularly limited but is preferably in a range from 50 to 99 wt. % and more preferably in a range from 80 to 90 wt. % of the entire mixture.

(C) Oil Agent

The oil agent used in the powder-in-oil dispersion and the like according to the present invention preferably is one or more oil agent selected from a silicone oil, a nonpolar organic compound, and a low polarity organic compound that are liquid from 5 to 100° C. A hydrocarbon oil and a fatty acid ester oil are preferable as the nonpolar organic compound and the low polarity organic compound. These are components that are particularly widely used as base materials for make-up cosmetic compositions, but it is possible to additionally use one or more type of compound selected from among publicly known vegetable oils and fats, animal oils and fats, higher alcohols, liquid fatty acid triglycerides, artificial sebum, and fluorine-based oils as well as these oil agents. The co-modified organopolysiloxane also displays superior dispersibility in these non-silicone-based oil agents and, therefore the hydrocarbon oil and the fatty acid ester oil can be stably compounded in a cosmetic composition and moisturizing characteristics imparted by these non-silicone-based oil agents can be maintained. Thus, the co-modified organopolysiloxane can improve stability over time of these non-silicone-based oil agent in a cosmetic composition. In particular, the co-modified organopolysiloxane according to the present invention has much better compatibility with hydrocarbon oils such as isododecane or isohexadecane than conventionally known polyether-modified silicones, which yields the advantage that the desired dispersibility and compounding stability can be further improved not only for conventional silicone-based formulations, but also for hydrocarbon solvent-based formulations.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition of the present invention. Moreover, there is a benefit in that stability over time of the cosmetic composition will not be negatively affected. Furthermore, with a cosmetic composition comprising the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non silicone-based oil agent (e.g. a hydrocarbon oil, a fatty acid ester oil, or the like), the cosmetic composition comprising a non silicone-based oil agent along with a silicone oil is advantageous in that a smoother, more luxurious tactile sensation is imparted.

These oil agents are the same as those disclosed by the applicants in paragraphs [0130] to [0135] and [0206] and so on in the above-mentioned Patent Document 5 (WO/2011/049248). Examples of the fluorine-based oil include perfluoropolyether, perfluorodecalin, perfluorooctane, and the like.

A compounded amount of the oil agent in the powder-in-oil dispersion of the present invention is not particularly limited but is preferably in a range from 0.1 to 50 wt. % and more preferably in a range from 0.5 to 25 wt. % in the raw material for use in cosmetic compositions.

The co-modified organopolysiloxane and the powder composition or the powder-in-oil dispersion comprising the co-modified organopolysiloxane can be suitably used as a preparation for external use, particularly for a cosmetic composition or a cosmetic raw material. Such preparations for external use, particularly cosmetic compositions or medicaments are within the scope of the present invention.

Particularly, the co-modified organopolysiloxane and the powder composition or the powder-in-oil dispersion comprising the co-modified organopolysiloxane can be advantageously used as a make-up cosmetic composition raw material. Such make-up cosmetic compositions comprising the co-modified organopolysiloxane and the powder composition or the powder-in-oil dispersion comprising the co-modified organopolysiloxane particularly are within the scope of the preferable embodiments of the present invention.

Water (D) can be further compounded in the cosmetic composition of the present invention and, thereby, the cosmetic composition of the present invention may take the form of an oil-in-water emulsion or a water-in-oil emulsion. In this case, the cosmetic composition of the present invention displays superior emulsion stability and sensation during use. The preparation of a hydrous cosmetic composition or emulsion cosmetic composition is the same as that disclosed by the applicants in paragraphs [0128] to [0146] in the above-mentioned Patent Document 5 (WO/2011/049248).

A uniformly soluble product (emulsion premix) that is the cosmetic raw material is formed by mixing the co-modified organopolysiloxane with the powder and the oil agent optionally in the presence of ethanol or a similar alcohol. The premix is mixed with water using the device described above. Thus, a cosmetic composition in the form of a uniform oil-in-water emulsion or water-in-oil emulsion can be produced.

The cosmetic composition of the present invention can further comprise (E) other surfactants. These other surfactants are components that function as cleansing components of the skin or the hair or, alternatively, as the oil agent or an emulsifier, and can be selected as desired depending on the type and function of the cosmetic composition. More specifically, the other surfactants can be selected from the group consisting of an anionic surfactant, a cationic surfactant, a nonionic surfactant, an amphoteric surfactant, and a semipolar surfactant. Preferably a silicone-based nonionic surfactant is used in combination.

These surfactants are the same as those disclosed by the applicants in paragraphs [0162], [0163] and [0195] to [0201] and so on in the above-mentioned Patent Document 5 (WO/2011/049248). The co-modified organopolysiloxane used in the present invention has a hydrophilic moiety and a hydrophobic moiety in the molecule and, therefore, has functionality as a dispersing agent. Thus, in cases where used in combination with a silicone-based nonionic surfactant, the component (A) functions as an aid to enhance the stability of the nonionic surfactant and may improve overall stability of the formulation. Particularly, the co-modified organopolysiloxane is preferably used in combination with polyoxyalkylene-modified silicones, polyglyceryl-modified silicones, glyceryl-modified silicones, and sugar alcohol-modified silicones. Moreover, the silicone-based nonionic surfactants described above in which an alkyl branch, a straight chain silicone branch, a siloxane dendrimer branch, or the like is (as desired) provided with the hydrophilic group can be advantageously used.

Depending on the purpose thereof, the cosmetic composition of the present invention can comprise one or two or more polyhydric alcohols and/or lower monohydric alcohols as a component (F). These alcohols are the same as those disclosed by the applicants in paragraphs [0159] and [0160] and so on in the above-mentioned Patent Document 5 (WO/2011/049248).

Depending on the purpose thereof, the cosmetic composition of the present invention can comprise one or two or more inorganic salts and/or organic salts as a component (G). These salts are the same as those disclosed by the applicants in paragraph [0161] and so on in the above-mentioned Patent Document 5 (WO/2011/049248).

Depending on the purpose thereof, the cosmetic composition of the present invention can include at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax as a component (H). These silicone components are the same as those disclosed by the applicants in paragraphs [0161] to [0193] and so on in the above-mentioned Patent Document 5 (WO/2011/049248). Examples of the component (H) other than those recited in Patent Document 5 include (H-1): a silicone polyester elastomer gel described in WO/2007/109240 and WO/2009/006091 in which compatibility with various components is enhanced and stable thickening effects are displayed as a result of introducing a polyoxypropylene group. Examples of commercially available products thereof include Dow Corning EL-8050 ID SILICONE ORGANIC ELASTOMER BLEND, Dow Corning EL-8051 IN SILICONE ORGANIC ELASTOMER BLEND, Dow Corning EL-7040 HYDRO ELASTOMER BLEND; and (H-2): PITUITOUS SILICONE FLUIDS described in WO/2011/028765 and WO/2011/028770. At least one type selected from these products can be used depending on the purpose of the cosmetic composition of the present invention. Furthermore, the liquid and slightly-crosslinkable organopolysiloxane proposed in Japanese Patent Application No. 2010-289722 and the domestic priority claimed therefrom (filed by the present applicant) can be used in the present invention.

The cosmetic composition of the present invention can, depending on the purpose of the cosmetic composition, comprise one or two or more water-soluble polymers as a component (J). These water-soluble polymers are the same as those disclosed by the applicants in paragraphs and so on in the above-mentioned Patent Document 5 (WO/2011/049248).

Depending on the purpose thereof, the cosmetic composition of the present invention can include one or two or more ultraviolet light blocking components as a component (K). These ultraviolet light blocking components are the same as the organic and inorganic ultraviolet light blocking components disclosed by the applicants in paragraphs [0202] to [0204] and so on in the above-mentioned Patent Document 5 (WO/2011/049248). The ultraviolet light blocking components that can be used particularly preferably include at least one type selected from among the group comprising fine particulate titanium oxide, fine particulate zinc oxide, paramethoxy cinnamic acid 2-ethylhexyl, 4-tert-butyl-4'-methoxydibenzoylmethane, diethylamino hydroxybenzoyl hexyl benzoate, benzotriazole-based ultraviolet radiation absorbers, and triazine-based ultraviolet radiation absorbers such as 2,4,6-tris[4-(2-ethylhexyloxycarbonyl)anilino]1,3,5-triazine {INCI: octyl triazone}, 2,4-bis{[4-(2-ethyl-hexyloxy)-2-hydroxy]phenyl}-6-(4-methoxyphenyl)-1,3,5-triazine {INCI: bis-ethylhexyloxyphenol methoxyphenyltriazine (product name: Tinosorb S™)}. These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

In the cosmetic composition of the present invention, by using the raw material for use in cosmetic compositions comprising the co-modified organopolysiloxane and the ultraviolet light blocking component together, the ultraviolet light blocking component can be stably dispersed in the cosmetic composition and the tactile sensation and the storage stability of the entire cosmetic composition can be improved. Therefore, superior UV blocking capacity can be imparted to the cosmetic composition.

In the cosmetic composition of the present invention, a total compounded amount of the ultraviolet light blocking component with respect to the entire cosmetic composition is in a range from 0.1 to 40.0 wt. % (mass %), and more preferably in a range from 0.5 to 15.0 wt. % (mass %).

Various components other than the components described above can be used in the cosmetic composition of the present invention, provided that such use does not impair the effects of the present invention. Examples thereof include oil-soluble gelling agents, organo-modified clay minerals, preservatives, bioactive components, skin beautifying components, pH adjusting agents, antioxidants, solvents, chelating agents, moisturizing components, perfumes, and the like. These optional cosmetic product components are the same as those disclosed by the applicants in paragraphs [0207], [0208] and [0220] to [0228] and so on in the above-mentioned Patent Document 5 (WO/2011/049248).

Additionally, in cases where the cosmetic composition according to the present invention is an anti-perspirant, or depending on the purpose of the cosmetic composition, the cosmetic composition can contain an anti-perspiration active component and/or a deodorant agent. These anti-perspiration components and deodorant components are the same as those disclosed by the applicants in paragraphs [0209] to [0219] and so on in the above-mentioned Patent Document 5 (WO/2011/049248). Similarly, in cases in which the cosmetic composition according to the present invention is an anti-perspirant composition, the preparation and method of use of the various anti-perspirant compositions are the same as those disclosed by the applicants in paragraphs [0234] to [0275] and so on of the above-mentioned Patent Document 5 (WO/2011/049248).

The external use preparation according to the present invention is not particularly limited, provided that it is a composition for application to the human body as a cosmetic composition or a medicament. Specific examples of cosmetic composition products of the present invention include skin cleansing agent products, skin care products, makeup products, anti-perspirant products, ultraviolet light blocking products, and similar skin use cosmetic products; hair use cleansing agent products, hair dressing products, hair use coloration products, hair growth products, hair rinsing products, hair conditioning products, hair treatment products, and similar hair use cosmetic products; and bath use cosmetic products. Examples of the medicament of the present invention include hair regrowth agents, hair growth promoters, analgesics, germicides, anti-inflammatory agents, refreshing agents, and skin anti-aging agents, but are not limited thereto.

The types, forms, and containers of the preparation for external use according to the present invention are the same as those recited in paragraphs [0230] to [0233] and the like of Patent Document 5 (WO/2011/049248, filed by the present applicant), but the co-modified organopolysiloxane is particularly useful as a raw material for various make-up cosmetic compositions. Additionally, the cosmetic composition according to the present invention is most advantageous as a make-up cosmetic composition comprising the co-modified organopolysiloxane (A), the powder or colorant (B), and the silicone oil, nonpolar organic compound, or low polarity organic compound (C) that is liquid from 5 to 100° C.

Specific examples of the make-up cosmetic composition include cleansing gels, cleansing creams, cleansing foams, cleansing milks, cleansing lotions, face washing creams, eye makeup removers, face washing foams, liquid soaps (body soaps), hand soaps, gel-like soaps, bar soaps, facial rinses, body rinses, shaving creams, removers, acne treatment cosmetics, and similar skin cleansing agent products; skin creams, scalp treatments, skin milks, milk lotions, emulsions, toners, moisturizing liquids, beautifying liquids, facial packs, body powders, essences, shaving lotions, massage lotions, and similar skin care products; foundations, liquid foundations, oil-based foundations, makeup bases, powders, face powders, lipsticks, lip creams, muddy colored lipsticks or rouges, lip glosses, eye shadows, eye liners, eye creams, eyebrow pencils, eyelash cosmetic products, eyebrow pencils, eyebrow blushes, mascaras, blushers, cheek cosmetics (cheek color, cheek rouge), manicures, pedicures, nail colors, nail laquers, enamel removers, nail polishes, and similar makeup products; deodorants and similar anti-perspirants; and sunscreen agents, tanning use medicaments (sun tanning agent), and similar ultraviolet light blocking products.

EXAMPLES

Hereinafter, the present invention is described in detail with reference to working examples and comparative examples, but it should be understood that the present invention is not limited to these working examples. The viscosity (dynamic viscosity) values are measured at 25° C. In the following compositional formulas, Me$_3$SiO groups (or Me$_3$Si group) are notated as "M", Me$_2$SiO groups are notated as "D", and MeHSiO groups are notated as "D$^H$". Units in which a methyl group in D is modified by any substituent is notated as D$^R$.

In the following working examples and the like, the number average molecular weight of the organopolysiloxane is the number average molecular weight based on the number average molecular weight in terms of standard polystyrene determined by gel permeation chromatography (GPC) with using the following analysis device and is measured under the following conditions.
Measurement temperature: 40° C. (column oven temperature)
Sample: organopolysiloxane is used as a 1 wt. % toluene solution
Detector: RI detector
Polymer for calibration curve: standard polystyrene Working Example 1

<Synthesis of Co-Modified Organopolysiloxane Compound P1>

First, 31.8 g of 1-hexadecene and 16.1 g of allyl polyether represented by CH$_2$=CH$_2$CH$_2$O—(C$_2$H$_4$O)$_{10}$—H were charged into 52.2 g of methylhydrogenpolysiloxane represented by the average composition formula MD$_{22}$D$^H_{6.9}$M in a reaction vessel in a stepwise manner in 30 g of toluene in the presence of 0.05 g of a platinum catalyst, and a reaction was performed for ten hours at 75 to 90° C. while stirring under a nitrogen air flow. The completion of the reaction was confirmed by an alkali decomposition gas generation method (i.e., the remaining Si—H groups are decomposed using a KOH ethanol/water solution, and the reaction rate is calculated from the volume of the produced hydrogen gas). After low-boiling-point matter was distilled out by heating the reaction solution at 90° C. under reduced pressure, the reaction solution was filtered to obtain 84 g of a co-modified organopolysiloxane represented by the average composition formula MD$_{22}$D$^{R1}_{6.2}$D$^{R2}_{0.7}$M.

In the formula, R$^1$ and R$^2$ are the structures indicated below.
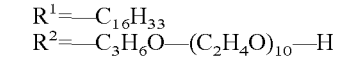
R$^2$=—C$_3$H$_6$O—(C$_2$H$_4$O)$_{10}$—H Working Example 2

<Synthesis of Co-Modified Organopolysiloxane Compound P2>

First, 26.2 g of 1-hexadecene and 18.9 g of allyl polyether represented by CH$_2$=CH$_2$CH$_2$O—(C$_2$H$_4$O)$_{10}$—H were charged into 45 g of methylhydrogenpolysiloxane represented by the average composition formula MD$_{22}$D$^H_{69}$M in a reaction vessel in a stepwise manner in 27 g of toluene in the presence of 0.025 g of a platinum catalyst, and a reaction was performed for ten hours at 75 to 90° C. while stirring under a nitrogen air flow. The completion of the reaction was confirmed by an alkali decomposition gas generation method (i.e., the remaining Si—H groups are decomposed using a KOH ethanol/water solution, and the reaction rate is calculated from the volume of the produced hydrogen gas). After low-boiling-point matter was distilled out by heating the reaction solution at 90° C. under reduced pressure, the reaction solution was filtered to obtain 71.4 g of a co-modified organopolysiloxane represented by the average composition formula MD$_{22}$D$^{R1}_{5.9}$D$^{R2}_1$M. In the formula, R$^1$ and R$^2$ are synonymous with the structures described above.

Working Example 3

<Synthesis of Co-Modified Organopolysiloxane Compound P3>

First, 22.7 g of 1-hexadecene and 29.5 g of allyl polyether represented by CH$_2$=CH$_2$CH$_2$O—(C$_2$H$_4$O)$_{10}$—H were charged into 47.9 g of methylhydrogenpolysiloxane represented by the average composition formula MD$_{22}$D$^H_{69}$M in a reaction vessel in a stepwise manner in 30 g of toluene in the presence of 0.025 g of a platinum catalyst, and a reaction was performed for ten hours at 75 to 90° C. while stirring under a nitrogen air flow. The completion of the reaction was confirmed by an alkali decomposition gas generation method (i.e., the remaining Si—H groups are decomposed using a KOH ethanol/water solution, and the reaction rate is calculated from the volume of the produced hydrogen gas). After low-boiling-point matter was distilled out by heating the reaction solution at 90° C. under reduced pressure, the reaction solution was filtered to obtain 81.4 g of a co-modified organopolysiloxane represented by the average composition formula MD$_{22}$D$^{R1}_{5.3}$D$^{R2}_{1.6}$M. In the formula, R$^1$ and R$^2$ are synonymous with the structures described above.

Working Example 4

<Synthesis of Co-Modified Organopolysiloxane Compound P4>

First, 32.1 g of 1-hexadecene and 63.5 g of allyl polyether represented by CH$_2$=CH$_2$CH$_2$O—(C$_2$H$_4$O)$_{10}$—H were charged into 104.4 g of methylhydrogenpolysiloxane represented by the average composition formula MD$_{22}$D$^H_{6.9}$M in a reaction vessel in a stepwise manner in 60 g of toluene in the presence of 0.05 g of a platinum catalyst, and a reaction was performed for ten hours at 75 to 90° C. while stirring under a nitrogen air flow. The completion of the reaction was confirmed by an alkali decomposition gas generation method (i.e., the remaining Si—H groups are decomposed using a KOH ethanol/water solution, and the reaction rate is calculated from the volume of the produced hydrogen gas). After low-boiling-point matter was distilled out by heating the reaction solution at 90° C. under reduced pressure, the reaction solution was filtered to obtain 166.4 g of a co-modified organopolysiloxane represented by the average composition formula $MD_{22}D^{R1}_{4.4}D^{R2}_{2.5}M$. In the formula, $R^1$ and $R^2$ are synonymous with the structures described above.

Working Example 5

<Synthesis of Co-Modified Organopolysiloxane Compound P5>

First, 45.9 g of 1-hexadecene and 55.3 g of allyl polyether represented by $CH_2=CH_2CH_2O-(C_2H_4O)_{10}-H$ were charged into 98.8 g of methylhydrogenpolysiloxane represented by the average composition formula $MD_{19}D^H_{6.1}M$ in a reaction vessel in a stepwise manner in 40 g of toluene in the presence of 0.05 g of a platinum catalyst, and a reaction was performed for ten hours at 75 to 90° C. while stirring under a nitrogen air flow. The completion of the reaction was confirmed by an alkali decomposition gas generation method (i.e., the remaining Si—H groups are decomposed using a KOH ethanol/water solution, and the reaction rate is calculated from the volume of the produced hydrogen gas). After low-boiling-point matter was distilled out by heating the reaction solution at 90° C. under reduced pressure, the reaction solution was subjected to acid treatment with a sodium bisulfate solution and filtration to obtain 184 g of a co-modified organopolysiloxane represented by the average composition formula $MD_{19}D^{R1}_{5}D^{R2}_{1.1}M$. In the formula, $R^1$ and $R^2$ are synonymous with the structures described above.

Working Example 6

<Synthesis of Co-Modified Organopolysiloxane Compound P6>

First, 45.9 g of 1-hexadecene and 55.3 g of allyl polyether represented by $CH_2=CH_2CH_2O-(C_2H_4O)_{10}-H$ were charged into 98.8 g of methylhydrogenpolysiloxane represented by the average composition formula $MD_{19}D^H_{6.1}M$ in a reaction vessel in a stepwise manner in 40 g of toluene in the presence of 0.05 g of a platinum catalyst, and a reaction was performed for ten hours at 75 to 90° C. while stirring under a nitrogen air flow. The completion of the reaction was confirmed by an alkali decomposition gas generation method (i.e., the remaining Si—H groups are decomposed using a KOH ethanol/water solution, and the reaction rate is calculated from the volume of the produced hydrogen gas). After low-boiling-point matter was distilled out by heating the reaction solution at 90° C. under reduced pressure, the reaction solution was subjected to hydrogenation with stabilized nickel: N103K (made by JGC C&C) and filtration to obtain 122 g of a co-modified organopolysiloxane represented by the average composition formula $MD_{19}D^{R1}_{5}D^{R2}_{1.1}M$. In the formula, $R^1$ and $R^2$ are synonymous with the structures described above.

<Organopolysiloxane Compound C1>

The organopolysiloxane compound C1 used in the comparative examples is an organopolysiloxane having a number average molecular weight of approximately 13,500 represented by the average composition formula $MD_{63}D^{R1}_{23}D^{R3}_{5}M$. This compound C1 can be easily synthesized with the same method as that of the embodiments described above using methylhydrogenpolysiloxane represented by the average composition formula $MD_{63}D^H_{28}M$, 1-hexadecene, and allyl polyether represented by $CH_2=CH_2CH_2O-(C_2H_4O)_{7}-H$ as raw materials.

<Organopolysiloxane Compound C2>

The organopolysiloxane compound C2 used in the comparative examples is an organopolysiloxane having a number average molecular weight of approximately 4600 represented by the average composition formula $MD_{45}D^{R2}_{2}M$. This compound C2 can be easily synthesized with the same method as that of the embodiments described above using methylhydrogenpolysiloxane represented by the average composition formula $MD_{45}D^H_{2}M$ and allyl polyether represented by $CH_2=CH_2CH_2O-(C_2H_4O)_{10}-H$ as raw materials.

The average composition formulae and number average molecular weights of the "co-modified organopolysiloxane compounds P1" to "P6" of the present invention and the "comparative co-modified compounds C1" and "C2" of the comparative examples, which were synthesized with the methods described above, are collectively shown in Table 1.

TABLE 1

| | Average composition formula | Molecular weight | Viscosity (mPa · s) |
|---|---|---|---|
| Co-modified organopolysiloxane | | | |
| P1 | $MD_{22}D^{R1}_{6.2}D^{R2}_{0.7}M$ | 3900 | 390 |
| P2 | $MD_{22}D^{R1}_{5.9}D^{R2}_{1}M$ | 4000 | 640 |
| P3 | $MD_{22}D^{R1}_{5.3}D^{R2}_{1.6}M$ | 4200 | 660 |
| P4 | $MD_{22}D^{R1}_{4.4}D^{R2}_{2.5}M$ | 4400 | 1000 |
| P5 | $MD_{19}D^{R1}_{5}D^{R2}_{1.1}M$ | 3600 | 480 |
| P6 | $MD_{19}D^{R1}_{5}D^{R2}_{1.1}M$ | 3600 | 400 |
| Organopolysiloxane for comparison | | | |
| C1 | $MD_{63}D^{R1}_{23}D^{R3}_{5}M$ | 13500 | 400 |
| C2 | $MD_{45}D^{R2}_{2}M$ | 4600 | 900 |

In the table, the structures and types of the functional groups are as follows.
$R^1 = -C_{16}H_{33}$
$R^2 = -C_3H_6O-(C_2H_4O)_{10}-H$
$R^3 = -C_3H_6O-(C_2H_4O)_{7}-H$

[Evaluation of Dispersion Stability]

Slurry-like microparticle dispersions were prepared according to the formulations and preparation methods shown in Preparation of dispersion 1 to Preparation of dispersion 16 below. These microparticle dispersions were then evaluated from the standpoints of dispersion characteristics and change in viscosity with time. A level of 1,000 mPa·s was used as a standard for the viscosities of the slurries, and those that had viscosities lower than 1,000 mPa·s were considered to be "low viscosity", while those that had viscosities equal to or greater than 1,000 m Pa·s were considered to be "high viscosity". Additionally, in cases where the slurry gelified after agitating using a paint shaker in the stage of producing the slurry, the product was labeled "slurry production impossible". The results are shown in Table 2. The components used in the preparation of each dispersion are as follows.

(1) Micro-particle powder: fine particulate titanium oxide
    Product name: MT-01 (manufactured by Tayca Corporation)
    Particle size: 10 nm (2) Fine particle powder: fine particulate zinc oxide
   Product name: FINEX-30S-LPT (manufactured by Sakai Chemical Corporation)
   Particle size: 35 nm
(3) Dispersion medium: isohexadecane
   Product name: ISOHEXADECANE (manufactured by Lanxess Corporation)

Working Example

Preparation of Dispersion 1

First, 20 g of fine particulate titanium oxide, 5 g of the co-modified organopolysiloxane (P1) of Working Example 1, and 25 g of isohexadecane were mixed, and 200 g of zirconia beads (0.8 mm φ) were added and mixed for 15 hours with a paint shaker (made by Asada Iron Works, Co., Ltd.) to form a slurry-like dispersion (TP1).

Working Example

Preparation of Dispersion 2

A slurry-like dispersion (TP2) was produced the same as in the preparation of dispersion 1, except that the co-modified organopolysiloxane (P2) of Working Example 2 was used in place of the co-modified organopolysiloxane (P1) of Working Example 1.

Working Example

Preparation of Dispersion 3

A slurry-like dispersion (TP3) was produced the same as in the preparation of dispersion 1, except that the co-modified organopolysiloxane (P3) of Working Example 3 was used in place of the co-modified organopolysiloxane (P1) of Working Example 1.

Working Example

Preparation of Dispersion 4

A slurry-like dispersion (TP4) was produced the same as in the preparation of dispersion 1, except that the co-modified organopolysiloxane (P4) of Working Example 4 was used in place of the co-modified organopolysiloxane (P1) of Working Example 1.

Working Example

Preparation of Dispersion 5

A slurry-like dispersion (TP5) was produced the same as in the preparation of dispersion 1, except that the co-modified organopolysiloxane (P5) of Working Example 5 was used in place of the co-modified organopolysiloxane (P1) of Working Example 1.

Working Example

Preparation of Dispersion 6

A slurry-like dispersion (TP6) was produced the same as in the preparation of dispersion 1, except that the co-modified organopolysiloxane (P6) of Working Example 6 was used in place of the co-modified organopolysiloxane (P1) of Working Example 1.

Comparative Example

Preparation of Dispersion 7

A slurry-like dispersion (TR1) was produced the same as in the preparation of dispersion 1, except that the co-modified organopolysiloxane (C1) of Comparative Example 1 was used in place of the co-modified organopolysiloxane (P1) of Working Example 1.

Comparative Example

Preparation of Dispersion 8

A slurry-like dispersion (TR2) was produced the same as in the preparation of dispersion 1, except that the co-modified organopolysiloxane (C2) of Comparative Example 2 was used in place of the co-modified organopolysiloxane (P1) of Working Example 1.

Working Example

Preparation of Dispersion 9

First, 30 g of fine particulate zinc oxide, 2.5 g of the co-modified organopolysiloxane (P1) of Working Example 1, and 17.5 g of isohexadecane were mixed, and 200 g of zirconia beads (0.8 mm φ) were added and mixed for 15 hours with a paint shaker to form a slurry-like dispersion (ZP1).

Working Example

Preparation of Dispersion 10

A slurry-like dispersion (ZP2) was produced the same as in the preparation of dispersion 9, except that the co-modified organopolysiloxane (P2) of Working Example 2 was used in place of the co-modified organopolysiloxane (P1) of Working Example 1.

Working Example

Preparation of Dispersion 11

A slurry-like dispersion (ZP3) was produced the same as in the preparation of dispersion 9, except that the co-modified organopolysiloxane (P3) of Working Example 3 was used in place of the co-modified organopolysiloxane (P1) of Working Example 1.

Working Example

Preparation of Dispersion 12

A slurry-like dispersion (ZP4) was produced the same as in the preparation of dispersion 9, except that the co-modified organopolysiloxane (P4) of Working Example 4 was used in place of the co-modified organopolysiloxane (P1) of Working Example 1.

Working Example

Preparation of Dispersion 13

A slurry-like dispersion (ZP5) was produced the same as in the preparation of dispersion 9, except that the co-modified organopolysiloxane (P5) of Working Example 5 was used in place of the co-modified organopolysiloxane (P1) of Working Example 1.

Working Example

Preparation of Dispersion 14

A slurry-like dispersion (ZP6) was produced the same as in the preparation of dispersion 9, except that the co-modified organopolysiloxane (P6) of Working Example 6 was used in place of the co-modified organopolysiloxane (P1) of Working Example 1.

Comparative Example

Preparation of Dispersion 15

A slurry-like dispersion (ZC1) was produced the same as in the preparation of dispersion 9, except that the co-modified organopolysiloxane (C1) of Comparative Example 1 was used in place of the co-modified organopolysiloxane (P1) of Working Example 1.

Comparative Example

Preparation of Dispersion 16

A slurry-like dispersion (ZC2) was produced the same as in the preparation of dispersion 9, except that the co-modified organopolysiloxane (C2) of Comparative Example 2 was used in place of the co-modified organopolysiloxane (P1) of Working Example 1.

TABLE 2

| Sample | | Titanium oxide slurry | Evaluation | Zinc oxide slurry | Evaluation |
|---|---|---|---|---|---|
| Working Examples | P1 | TP1 | ∘∘ | ZP1 | Δ∘ |
| | P2 | TP2 | ∘∘ | ZP2 | ∘∘ |
| | P3 | TP3 | ∘∘ | ZP3 | ∘∘ |
| | P4 | TP4 | ∘∘ | ZP4 | ∘∘ |
| | P5 | TP5 | ∘∘ | ZP5 | Δ∘ |
| | P6 | TP6 | ∘∘ | ZP6 | ∘∘ |
| Comparative Examples | C1 | TC1 | ΔΔ | ZC1 | ∘x |
| | C2 | TC2 | ∘Δ | ZC2 | x— |

Evaluation standards are as follows.
∘∘: Low viscosity slurry producible, no increase in viscosity with time
∘Δ: Low-viscosity slurry producible, increase in viscosity with time
∘x: Low viscosity slurry producible, gelling with time
Δ∘: High viscosity slurry producible, reduction in viscosity with time
ΔΔ: High-viscosity slurry producible, increase in viscosity with time
x—: Slurry production impossible As shown in Table 2, with the novel co-modified organopolysiloxanes P1 to P6 according to the present invention, it was possible to produce a slurry as a powder-in-oil dispersion using isohexadecane, which is a typical hydrocarbon oil, with both titanium oxide and zinc oxide were used. In contrast, in the comparative compounds C1 and C2, when fine particulate zinc oxide was used, in particular, it was not possible to produce a slurry with excellent stability over time under the same conditions as those of the co-modified organopolysiloxane according to the present invention, and marked differences were observed in the performance as a powder treatment agent. In addition, when titanium oxide was used, it was possible to produce a slurry even with the comparative organopolysiloxanes, but the overall performance was inferior to powder-in-oil dispersions using the novel co-modified organopolysiloxane according to the present invention, as indicated by increases in viscosity at the time of production and increases in viscosity over time. These results demonstrate that even with the same polyether-modified silicone, the performance varies substantially depending on the manner in which the structure is controlled, such as the molecular weight or the presence or absence of long-chain alkyl groups. That is, the product of the present invention has a lower molecular weight than conventional products and a structure that is precisely controlled, so even when isohexadecane, which is a hydrocarbon oil, is used, high efficiency and performance are exhibited with respect to titanium oxide and zinc oxide, which is likely why it was possible to form a slurry.

Formulation Examples

Hereinafter the cosmetic composition of the present invention will be described using working examples based on the following specific formulations, but the cosmetic composition of the present invention is not limited to the types or compositions described in the formulations indicated in these working examples. Note that in the formulations, "part(s)" refers to parts by weight (mass).
Formulation Example 1: Liquid foundation (W/O type)
Formulation Example 2: Liquid foundation (O/W type)
Formulation Example 3: Sunscreen cream (W/O type)
Formulation Example 4: Sunscreen (shaking type)
Formulation Example 5: Base cream
Formulation Example 6: Rouge
Formulation Example 7: Liquid rouge
Formulation Example 8: Lipstick
Formulation Example 9: Lip gloss
Formulation Example 10: Eye shadow
Formulation Example 11: Mascara Formulation Example 1

Liquid Foundation (W/O Type)

(Components)

| | |
|---|---|
| 1. Isohexadecane | 20 parts |
| 2. Isododecane | 5 parts |
| 3. Dimethylsiloxane (2 cs) | 5 parts |
| 4. Isotridecyl isononanoate | 3 parts |
| 5. Glyceryl tricapryl-caprate | 2 parts |
| 6. Polyether-modified silicone (note 1) | 1.5 parts |
| 7. Co-modified organopolysiloxane P5 | 0.5 parts |
| 8. Organo-modified clay mineral (Bentone 38V) | 1.5 parts |
| 9. Octyl methoxycinnamate | 5 parts |
| 10. Octylsilane treated titanium oxide | 8.5 parts |
| 11. Octylsilane-treated red iron oxide | 0.4 parts |
| 12. Octylsilane-treated yellow iron oxide | 1 part |
| 13. Octylsilane treated black iron oxide | 0.1 parts |
| 14. Dimethicone crosspolymer (note 2) | 2 parts |
| 15. Isododecane/(acrylate/polytrimethylsiloxy methacrylate) copolymer (note 3) | 1 part |

-continued

| | |
|---|---|
| 16. 1,3-Butylene glycol | 5 parts |
| 17. Glycerin | 3 parts |
| 18. Sodium chloride | 0.5 parts |
| 19. Preservative | q.s. |
| 20. Purified water | Remainder |
| 21. Perfume | q.s. |

(note 1): DC-5200 manufactured by Dow Corning Co., Ltd. was used.
(note 2): EL-8051 manufactured by Dow Corning Co., Ltd. was used.
(note 3): FA4002ID Silicone Acrylate manufactured by Dow Corning Toray Co., Ltd. was used.

(Production Method)

Step 1: Components 1, 2, 3, 6, 8, 9, 14, and 15 were mixed while stirring.
Step 2: Components 4, 5, 7, and 10 to 13 were kneaded and mixed using a triple roller.
Step 3: The mixture obtained in step 2 was added to the mixture obtained in step 1 while agitating then agitated and mixed further.
Step 4: An aqueous phase in which components 16 to 21 are uniformly dissolved was added to the mixture obtained in Step 3 and emulsified. A container was filled with the emulsion to obtain a product.

The resulting W/O-type liquid foundation demonstrated excellent emulsion stability when used, excellent water resistance and cosmetic durability, excellent masking of skin imperfections and wrinkles, and excellent spread and adhesiveness.

Formulation Example 2

Liquid Foundation (O/W)

Components

| | |
|---|---|
| Carboxydecyl trisiloxane | 0.5 part |
| Stearic acid | 0.5 parts |
| 3. Polysorbate 80 | 1.2 parts |
| 4. Sorbitan sesquioleate | 0.2 parts |
| 5. Glyceryl stearate | 1.5 parts |
| 6. Behenyl alcohol | 2.0 parts |
| 7. Isohexadecane | 8 parts |
| 8. Dimethicone (6 cs) | 1 parts |
| 9. Squalane | 3 parts |
| 10. Trioctanoin | 3 parts |
| 11. Glyceryl tricapryl-caprate | 3 parts |
| 12. Co-modified organopolysiloxane P6 | 0.2 parts |
| 13. Octylsilane treated titanium oxide | 8.5 parts |
| 14. Octylsilane-treated red iron oxide | 0.4 parts |
| 15. Octylsilane-treated yellow iron oxide | 1 part |
| 16. Octylsilane treated black iron oxide | 0.1 parts |
| 17. 1,3-Butylene glycol | 8 parts |
| 18. Sodium hydroxide aqueous solution (1%) | 15 parts |
| 19. Carbomer (2%) | 10 parts |
| 20. Purified water | Remainder |

(Production Method)

Step 1: Components 1 to 8 were mixed while stirring.
Step 2: Components 9 to 16 were kneaded and mixed using a triple roller.
Step 3: The mixture obtained in step 2 was added to the mixture obtained in step 1 while agitating, then agitated and mixed further.
Step 4: An aqueous phase formed by uniformly dissolving components 17, 18, and 20 was added to the mixture obtained in step 3 and emulsified. After emulsification, component 19 was added and stirred, and a container was filled with the emulsion to obtain a product.

The resulting O/W-type liquid foundation demonstrated excellent emulsion stability when used, excellent water resistance and cosmetic durability, excellent masking of skin imperfections and wrinkles, and excellent spread and adhesiveness.

Formulation Example 3

Sunscreen Cream (W/O)

(Components)

| | |
|---|---|
| 1. Caprylyl methicone | 3.8 parts |
| 2. Isohexadecane | 6.7 parts |
| 3. Isotridecyl isononanoate | 4 parts |
| 4. Polyether-modified silicone (note 1) | 2 parts |
| 5. Dimethicone crosspolymer (note 2) | 1.5 parts |
| 6. Organomodified bentonite | 0.8 parts |
| 8. Zinc oxide slurry (60 wt. % zinc oxide) (note 3) | 35 parts |
| 9. Titanium oxide slurry (40 wt. % titanium oxide) (note 4) | 25 parts |
| 10. Isododecane/(acrylate/polytrimethylsiloxy methacrylate) copolymer (note 5) | 2.3 part |
| 11. Isododecane/trimethylsiloxysilic acid | 1 part |
| 12. 1,3-Butylene glycol | 2 parts |
| 13. Sodium citrate | 0.2 parts |
| 14. Sodium chloride | 0.5 parts |
| 15. Purified water | Remainder |

(note 1): ES-5300, manufactured by Dow Corning Toray Co., Ltd. was used.
(note 2): DC-8051, manufactured by Dow Corning Toray Co., Ltd. was used.
(note 3): Dispersion ZP6 described in the working examples was used.
(note 4): Dispersion TP6 described in the working examples was used.
(note 5): FA-4002ID, manufactured by Dow Corning Toray Co., Ltd. was used.

(Production Method)

Step 1: Mix Components 1 to 11.
Step 2: Mix Components 12 to 15.
Step 3: Add the aqueous phase obtained in Step 2 to the mixture obtained in Step 1 while agitating. After emulsifying, fill a container with the emulsion to obtain a product.

Formulation Example 3 is a sunscreen cream comprising a dispersion of an inorganic ultraviolet light blocking component treated using the co-modified polyorganosiloxane P3 according to the present invention. Even though this sunscreen cream has a high aqueous phase component content and contains an inorganic ultraviolet light blocking component, there is no separation of the oil components or the powder. Thus, this sunscreen cream can be kept in stock over an extended period of time at a temperature of around 40° C. (ambient temperature during summer) and stability over time is superior. Furthermore, when used, spreadability was excellent, stickiness was reduced and sensation during use was superior. The sunscreen cream was non-irritating, and long-lasting ultraviolet light protection effects were provided. There was no change in this excellent sensation during use from before storing at around 40° C. to after storing.

Formulation Example 4

Sunscreen (Shaking Type)

(Components)

| | |
|---|---|
| 1. Octyl methoxycinnamate | 8 parts |
| 2. Isotridecyl isononanoate | 7 parts |
| 3. Diethylamino hydroxybenzoyl hexyl benzoate | 2 parts |
| 4. Polyether-modified silicone (note 1) | 2 parts |

-continued

|   |   |
|---|---|
| 5. Titanium oxide slurry (note 2) | 5 parts |
| 5. Zinc oxide slurry (note 3) | 28 parts |
| 6. Isohexadecane | 18.2 parts |
| 7. Dimethicone crosspolymer | 3 parts |
| 8. Trimethylsiloxysilicic acid | 3.3 parts |
| 9. Preservative | 0.1 parts |
| 10. Ethanol | 5 parts |
| 11. 1,3-Butylene glycol | 3 parts |
| 12. Purified water | Remainder |

(note 1): DC-5200 manufactured by Dow Corning Co., Ltd. was used.
(note 2): Dispersion TP5 described in the working examples was used.
(note 3): Dispersion ZP5 described in the working examples was used.

(Production method)

Step 1: Mix Components 1 to 8.

Step 2: Add the mixture of components 9 to 12 to the mixture of step 1 and emulsify.

The obtained sunscreen had reduced stickiness and superior sensation during use when applied on skin, and provided lasting ultraviolet light protection effects.

Formulation Example 5

Base Cream (Components)

|   |   |
|---|---|
| 1. Caprylyl methicone | 2 parts |
| 2. Isohexadecane | 9 parts |
| 3. Light liquid paraffin | 3 parts |
| 4. Polyether-modified silicone (note 1) | 2 parts |
| 5. Ethylhexyl palmitate | 5 parts |
| 6. Co-modified organopolysiloxane P6 | 0.5 parts |
| 7. 2-Ethylhexyl para-methoxycinnamate | 2 parts |
| 8. Silicone elastomer (note 2) | 4 parts |
| 9. Octylsilane treated titanium oxide | 6 parts |
| 10. Octylsilane-treated red iron oxide | 0.3 parts |
| 11. Octylsilane-treated yellow iron oxide | 0.7 part |
| 12. Octylsilane treated black iron oxide | 0.07 parts |
| 13. Organomodified bentonite | 0.5 parts |
| 14. Barium sulfate | 2 parts |
| 15. Talc | 1 part |
| 16. Nylon powder | 3 parts |
| 17. Preservative | q.s. |
| 18. Xanthan gum | 0.1 parts |
| 19. L-Ascorbic acid magnesium phosphate ester | 0.3 parts |
| 20. Purified water | Remainder |

(note 1): ES-5300, manufactured by Dow Corning Toray Co., Ltd., was used.
(note 2): 9045 Silicone Elastomer Blend, manufactured by Dow Corning Corporation, was used.

(Production Method)

Step 1: Mix and disperse components 1 to 16.

Step 2: Mix Components 17 to 20.

Step 3: Add the mixture obtained in Step 2 to the mixture obtained in Step 1 and emulsify at room temperature. Fill a container with the emulsion to obtain a product.

This foundation cream demonstrated good spread, and excellent cosmetic film uniformity and adhesion to the skin. Additionally, skin imperfections, wrinkles, and pores were hardly noticeable. Moreover, the emulsion state of the base cream was stable.

Formulation Example 6

Rouge (Components)

|   |   |
|---|---|
| 1. Triethylhexanoin | 10.0 parts |
| 2. Ethylhexyl succinate | 13.5 parts |
| 3. Octyl sebacate | 3.5 parts |
| 3. Sorbitan sesquiisostearate | 4.0 parts |
| 4. Microcrystalline wax | 11.0 parts |
| 5. Paraffin wax | 15.7 parts |
| 6. Diisostearyl malate | 7.0 parts |
| 7. Glyceryl triisostearate | 9.0 parts |
| 8. Propylene glycol dicapyrlate | 7.0 parts |
| 9. Inulin stearate (product name: Rheopearl ISL2 manufactured by Chiba Flour Milling Co., Ltd.) | 2.0 parts |
| 10. Polyether-modified silicone (note 1) | 1 parts |
| 10. Co-modified organopolysiloxane P6 | 0.2 parts |
| 11. Isododecane/(acrylate/polytrimethylsiloxy methacrylate) copolymer (note 2) | 3.0 part |
| 12. Isododecane solution of trimethylsiloxysilicic acid (active ingredient: 40%) | 2.0 parts |
| 13. Yellow No. 4 | q.s |
| 14. Titanium oxide | 1.0 parts |
| 15. Black iron oxide | 1.0 parts |
| 16. Mica | 1.0 parts |
| 17. Red 104 | q.s |
| 18. Purified water | 7.0 parts |
| 19. 1,3-Butylene glycol | 1.0 parts |
| 20. Preservative | q.s. |
| 21. Perfume | q.s. |

(note 1): ES-5300, manufactured by Dow Corning Toray Co., Ltd. was used.
(note 2): FA-4002ID, manufactured by Dow Corning Toray Co., Ltd. was used.

(Production Method)

Step 1: Heat and dissolve components 1 to 17.

Step 2: Mix components 18 to 20.

Step 3: Add the mixture of Step 2 to the mixture of Step 1 and further agitate and mix.

Step 4: Add component 21 to the mixture of Step 3. Fill a closed vessel with the obtained mixture to obtain a product.

The rouge had a luxurious feel and excellent spreadability; could be applied uniformly to the lips; and could deliver a finish having superior luster and feeling of sheerness. Furthermore, there was no stickiness on the lips after application, and storage stability in cases where the product was stocked was excellent.

Formulation Example 7

Liquid Rouge (Components)

|   |   |
|---|---|
| 1. Isododecane/(acrylate/polytrimethylsiloxy methacrylate) copolymer (note 1) | 5 part |
| 2. Isododecane/trimethylsiloxysilic acid | 5 parts |
| 3. Phenylmethyl silicone | 10 parts |
| 4. Ethylhexyl palmitate | 10 parts |
| 3. Aerosol silicic anhydride | 0.1 parts |
| 4. Spherical urethane powder | 5 parts |
| 5. Co-modified organopolysiloxane P5 | 5 parts |
| 6. Octyl methoxycinnamate | 1 part |
| 7. Red No. 202 | 0.5 parts |
| 8. Titanium oxide | 0.5 parts |
| 9. Titanated mica | 3 parts |

-continued

| | | |
|---|---|---|
| 10. Perfume | 0.1 | parts |
| 11. Ethanol | 10 | parts |
| 15. Preservative | 0.2 | parts |
| 13. Sodium chloride | 0.1 | parts |
| 14. Purified water | 29.5 | parts |

(note 1): FA-4002ID, manufactured by Dow Corning Toray Co., Ltd. was used.

(Production Method)

A: Disperse and mix components 1 to 9.

B: Separately, dissolve components 10 to 14 uniformly.

C: Add B to A and emulsify. After defoaming, fill a container with the mixture to obtain a water-in-oil emulsion lipstick.

Formulation Example 8

Lipstick (Components)

| | |
|---|---|
| 1. Polyethylene-polypropylene copolymer | 5 parts |
| 2. Candelilla wax | 5 parts |
| 3. Carnauba wax | 5 parts |
| 4. Vaseline | 10 parts |
| 5. 2-Cetyl ethylhexanoate | 10 parts |
| 6. Diglycerin diisostearate | 14.5 parts |
| 7. Macadamia nut oil | 7 parts |
| 8. Inulin stearate (Rheopearl ISK2 manufactured by Chiba Flour Milling Co., Ltd.) | 23 parts |
| 9. Co-modified organopolysiloxane P4 | 1 parts |
| 10. Red No. 201 | 1 part |
| 11. Red No. 202 | 3 parts |
| 12. Yellow No. 4 aluminum lake | 3 parts |
| 13. Titanium oxide | 1 part |
| 14. Black iron oxide | 0.5 parts |
| 15. Iron oxide titanated mica | 10 parts |
| 16. Preservative | q.s. |
| 17. Perfume | q.s. |

(Production Method)

A: Heat and dissolve components 1 to 9. Then, add components 10 to 16 and mix uniformly.

B: Add Component 17 to A, and fill a container with the mixture to obtain a lipstick.

Formulation Example 9

Lip Gloss (Components)

| | |
|---|---|
| 1. Polyamide-modified silicone (note 1) | 10 parts |
| 2. Co-modified organopolysiloxane P4 | 1 parts |
| 3. Methyl phenyl-modified silicone | 28 parts |
| 4. Isononyl isononanoate | 38 parts |
| 5. Isohexadecane | 14 parts |
| 5. Trioctanoin | 2 parts |
| 6. Titanated mica | 3 parts |

(note 1): 2-8178 gallant manufactured by Dow Corning Corporation was used.

(Production Method)

After each component was heated and mixed at 100° C., a container was filled to obtain a product.

This lip gloss demonstrated good compatibility with oil-based raw materials, and the storage stability was good when the product was stocked.

Formulation Example 10

Eye Shadow (Components)

| | |
|---|---|
| 1. Isododecane | 13 parts |
| 2. Isohexadecane | 12 parts |
| 3. Squalane | 3 parts |
| 4. Co-modified organopolysiloxane P4 | 2 parts |
| 5. PEG (10) lauryl ether | 0.5 parts |
| 6. Octylsilane treated titanium oxide | 6.2 parts |
| 7. Octyl silane-treated sericite | 4 parts |
| 8. Octyl silane-treated mica | 6 parts |
| 9. Sodium chloride | 2 parts |
| 10. Propylene glycol | 8 parts |
| 11. Preservative | q.s. |
| 12. Perfume | q.s. |
| 13. Purified water | Remainder |

(Production Method)

A: Mix components 1 to 5, and then add and disperse uniformly components 6 to 8.

B: Dissolve components 9 to 13 uniformly.

C: B was gradually added to A and emulsified while stirring to obtain an eye shadow.

The obtained eye shadow spread smoothly when applying and had superior color development.

Formulation Example 11

Mascara (Components)

| | |
|---|---|
| 1. Paraffin wax | 5 parts |
| 2. Light liquid isoparaffin | Remainder |
| 3. Caprylyl methicone | 0.5 parts |
| 4. Co-modified organopolysiloxane P4 | 0.5 parts |
| 5. Trioctanoin | 13 parts |
| 6. Decamethyl cyclopentasiloxane | 20 parts |
| 7. Inulin stearate | 5 parts |
| 8. Cyclopentasiloxane, dimethicone crosspolymer (note 1) | 10 parts |
| 9. Fluorine compound surface-treated black iron oxide | 6 parts |
| 10. Sucrose fatty acid ester | 4 parts |
| 11. Beeswax | 5 parts |
| 12. Pentaerythrityl rosinate | 5 parts |
| 13. Preservative | q.s. |
| 14. Purified water | 5 parts |

(note 1): DC-9040, manufactured by Dow Corning Corporation, was used.

(Production Method)

After components 1 to 12 were dissolved while heating, the components were sufficiently mixed and dispersed. A mixture of components 13 and 14 was added to the solution and emulsified, and a container was filled to obtain a product.

The resulting mascara had a deep dark appearance and excellent sheen when used. In addition, the mascara demonstrated good adhesion to the eyelashes and an excellent eyelash curl volume effect which lasted a long time.

Products produced by replacing the components corresponding with silicone compounds Nos. 1 to 14 in the Formulation Examples of the cosmetic compositions recited in Patent Document 5 (WO/2011/049248, filed by the present applicant) with the co-modified organopolysiloxanes (co-modified organopolysiloxanes P1 to P6) according to the present invention are included in the scope of the present invention as Formulation Examples of cosmetic compositions according to the present invention.

Specifically, the aforementioned Patent Document 5 discloses emulsions, lip glosses, oil-based foundations, water-in-oil emulsion transparent anti-perspirant compositions, and non-aqueous stick-form anti-perspirant compositions as compositions that can be replaced by the co-modified organopolysiloxane according to the present invention, and paragraphs [0459] to
in the above-mentioned Patent Document 5 also disclose the following formulation examples.
[Example 1: Emulsion foundation]
[Example 2: Liquid foundation]
[Example 3: Foundation]
[Example 4: Water-in-oil cream]
[Example 5: Water-in-oil emulsion composition]
[Example 6: Water-in-oil emulsion rouge (liquid)]
[Example 7: Liquid rouge]
[Example 8: Rouge]
[Example 9: Sunscreen emulsion]
[Example 10: Emulsion]
[Example 11: UV blocking cream]
[Example 12: UV blocking water-in-oil emulsion]
[Example 13: Sunscreen agent]
[Example 14: Water-in-oil emulsion sunscreen]
[Example 15: O/W cream]
[Example 16: Eye shadow]
[Example 17: Mascara]
[Example 18: Mascara]
[Example 19: Solid powder eye shadow]
[Example 20: Pressed powder cosmetic]
[Example 21: Powder foundation]
[Example 22: Pressed foundation]
[Example 23: Cream]
[Example 24: Foundation]
[Example 25: Water-in-oil emulsion-type sunscreen]
[Example 26: Lipstick]
[Example 27: Rouge]
[Example 28: Foundation]
[Example 29: Anti-perspirant aerosolized cosmetic composition]
[Example 30: Nonaqueous pressurized anti-perspirant product]
[Example 31: Aerosol type anti-perspirant composition]
[Example 32: Anti-perspirant lotion composition]
[Example 33: W/O emulsion-type skin external use preparation]
[Example 34: Nonaqueous anti-perspirant deodorant stick composition]
[Example 35: W/O solid anti-perspirant stick composition]
[Example 36: W/O emulsion type anti-perspirant cream composition]
[Example 37: Mascara]
[Example 38: Aftershave cream]
[Example 39: Solid foundation]
[Example 40: Daytime use skin-lightening cream]
[Example 41: Sun tanning cream]
[Example 42: Polyol/O-type nonaqueous emulsion skin external use preparation]
[Example 43: Polyol/O-type nonaqueous emulsion skin external use preparation]

INDUSTRIAL APPLICABILITY

The co-modified organopolysiloxane according to the present invention has a relatively low molecular weight and excellent surface treatment performance, so the co-modified organopolysiloxane can be used in preparations for external use and, in particular, for industrial applications other than cosmetics. Examples thereof include varnishes or coating additives having superior heat resistance, weather resistance, or electrical properties; foam stabilizers or modifying agents for polyol base compounds used in various urethane and foam materials; debonding agents or release agents; antifoaming agents; grease or oil compounds; modifying agents, additives, or surface treatment agents use for oil, rubber, or resin of insulating, glazing, water repelling, heating mediums, cooling mediums, and lubricants; compounds, modifying agents, and precursors for silane coupling agents; coating materials or sealing materials for buildings or linings; protective agents, lubricants, or buffer agents for fiber optics and electrical wiring; and the like. However, the novel organopolysiloxane copolymer according to the present invention is not limited to such applications.

The invention claimed is:

1. A surface treatment agent or powder treatment agent, comprising:

a co-modified organopolysiloxane represented by general formula (1-1)

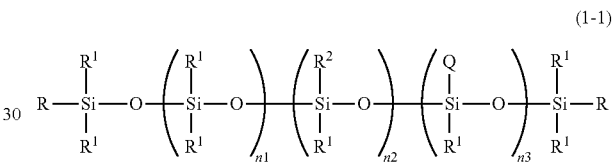

the co-modified organopolysiloxane having a number average molecular weight of less than 4500 in terms of equivalent polystyrene molecular weight as measured by gel permeation chromatography and having a long-chain alkyl group and a polyoxyalkylene group in the molecule;

wherein each $R^1$ is independently a substituted or unsubstituted monovalent hydrocarbon group having from 1 to 30 carbons, or a hydrogen atom;

each $R^2$ is independently a substituted or unsubstituted long-chain or branched monovalent hydrocarbon having from 6 to 30 carbons;

each R is a group selected from $R^1$, $R^2$, and Q; however, when n3 =0, at least one of the R moieties is Q; and Q is a hydrophilic group having a polyoxyalkylene group represented by the following structural formula (2)

wherein $R^3$ is an alkyl group having from 1 to 4 carbons or a hydrogen atom; r is a number in a range of from 0 to 100; s is a number in a range of from 0 to 50; and "r+s" is a number in a range of from 3 to 100; and (n1+n2+n3) is a number in a range of from 2 to 40; n1 is a number in a range of from 1 to 30; n2 is a number in a range of from 1 to 20; and n3 is a number in a range of from 0 to 50.

2. The surface treatment agent or powder treatment agent according to claim 1, wherein the co-modified organopolysiloxane is represented by the following structural formula (1-1-1)

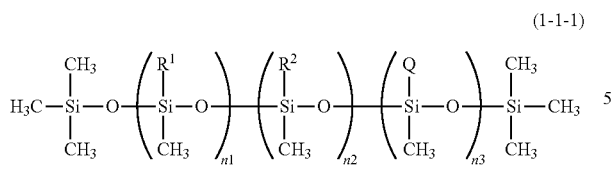

(1-1-1)

wherein R¹, R², and Q are defined above; (n1+n2+n3) is a number in a range of from 2.1 to 40; n1 is a number in a range of from 1 to 30; n2 is a number in a range of from 1 to 20; and n3 is a number in a range of from 0.1 to 5.

3. A powder composition, comprising:
(A) the surface treatment agent or powder treatment agent according to claim 1; and
(B) a powder or a coloring agent.

4. The powder composition according to claim 3, wherein the component
(B) is one or more selected from an inorganic pigment powder, an organic pigment powder, and a resin powder, each having an average diameter in a range of from 1 nm to 20 μm.

5. A cosmetic composition comprising the powder composition according to claim 3.

6. A powder-in-oil dispersion, comprising:
(A) the surface treatment agent or powder treatment agent according to claim 1;
(B) a powder or coloring agent; and
(C) one or more oil agents selected from a silicone oil, a nonpolar organic compound, or a low-polarity organic compound that is a liquid at 5 to 100° C.

7. A cosmetic composition comprising the powder-in-oil dispersion according to claim 6.

8. A powder-in-oil dispersion, comprising:
(A) the surface treatment agent or powder treatment agent according to claim 1;
(B) a powder or coloring agent; and
(C1) a hydrocarbon oil that is liquid at 5 to 100° C.

9. A preparation for external use comprising the surface treatment agent or powder treatment agent according to claim 1.

10. The preparation for external use according to claim 9 further defined as a cosmetic composition or a medicament.

11. A makeup cosmetic composition, comprising:
(A) the surface treatment agent or powder treatment agent according to claim 1;
(B) a powder or coloring agent; and
(C) a silicone oil, a nonpolar organic compound, or a low polarity organic compound that is liquid from 5° C. to 100° C.

12. A powder-in-oil dispersion, comprising:
a powder or coloring agent treated with the surface treatment agent or powder treatment agent according to claim 1; and
one or more oil agents selected from a silicone oil, a nonpolar organic compound, or a low-polarity organic compound that is a liquid at 5 to 100° C.

13. The surface treatment agent or powder treatment agent according to claim 1, wherein each R¹ is unsubstituted and each R² is unsubstituted.

14. A powder composition, comprising:
(A) the surface treatment agent or powder treatment agent according to claim 13; and
(B) a powder or a coloring agent.

15. A cosmetic composition comprising the powder composition according to claim 14.

16. A powder-in-oil dispersion, comprising:
(A) the surface treatment agent or powder treatment agent according to claim 13;
(B) a powder or coloring agent; and
(C) one or more oil agents selected from a silicone oil, a nonpolar organic compound, or a low-polarity organic compound that is a liquid at 5 to 100° C.

17. A cosmetic composition comprising the powder-in-oil dispersion according to claim 16.

18. A powder-in-oil dispersion, comprising:
(A) the surface treatment agent or powder treatment agent according to claim 13;
(B) a powder or coloring agent; and
(C1) a hydrocarbon oil that is liquid at 5 to 100° C.

19. A preparation for external use comprising the surface treatment agent or powder treatment agent according to claim 13.

20. A makeup cosmetic composition, comprising:
(A) the surface treatment agent or powder treatment agent according to claim 13;
(B) a powder or coloring agent; and
(C) a silicone oil, a nonpolar organic compound, or a low polarity organic compound that is liquid from 5° C. to 100° C.

* * * * *